(12) United States Patent
Tabuchi

(10) Patent No.: US 6,234,229 B1
(45) Date of Patent: May 22, 2001

(54) MANUFACUTURING EQUIPMENT FOR SANITARY NAPKINS WITH WINGS HAVING NO PEELING-OFF PAPER STRIPS

(75) Inventor: Kunihiro Tabuchi, Kagawa (JP)

(73) Assignee: Tao Machine Industry, Inc., Kagawa (JP)

( * ) Notice: Subject to any disclaimer, the term of this patent is extended or adjusted under 35 U.S.C. 154(b) by 0 days.

(21) Appl. No.: 09/236,344

(22) Filed: Jan. 25, 1999

(30) Foreign Application Priority Data

Aug. 5, 1998 (JP) ................................................ 10-221650

(51) Int. Cl.[7] ........................... B32B 31/04; B32B 31/10; B32B 31/16
(52) U.S. Cl. ........................ 156/464; 156/289; 156/443; 156/459
(58) Field of Search .............................. 604/385.02, 389; 206/438; 156/289, 464, 459, 443

(56) References Cited

FOREIGN PATENT DOCUMENTS

| | | |
|---|---|---|
| 3-184543 | 8/1991 | (JP) . |
| 6-26835 U | 4/1994 | (JP) . |
| 7-506037 | 7/1995 | (JP) . |
| 10-290819 | 11/1998 | (JP) . |

*Primary Examiner*—Adrienne C. Johnstone
(74) *Attorney, Agent, or Firm*—Arent Fox Kintner Plotkin & Kahn, PLLC

(57) ABSTRACT

A sanitary-napkin-product manufacturing equipment comprises (i) a manufacturing machine of a sanitary napkin with wings and (ii) a wrapping machine 100 to apply slip-preventing adhesive, which comes easily off silicone coats, to the back of the sanitary napkin and wrap the sanitary napkin in a wrapping film, of which the inside is coated with silicone, to produce a sanitary napkin product. The manufacturing machine comprises a facing-sheet-adhesive applying unit, an absorbent-body cutout unit, a lining-sheet-adhesive applying unit, a sandwiching unit, a heat-sealing unit, and a sanitary-napkin cutout unit. The wrapping machine comprises a longitudinally folding unit, a slip-preventing-adhesive applying unit, an overlaying unit, a wing-folding unit, a hold-down-tape affixing unit, a film-sealing unit, and a cutting unit.

9 Claims, 15 Drawing Sheets

F I G. 4
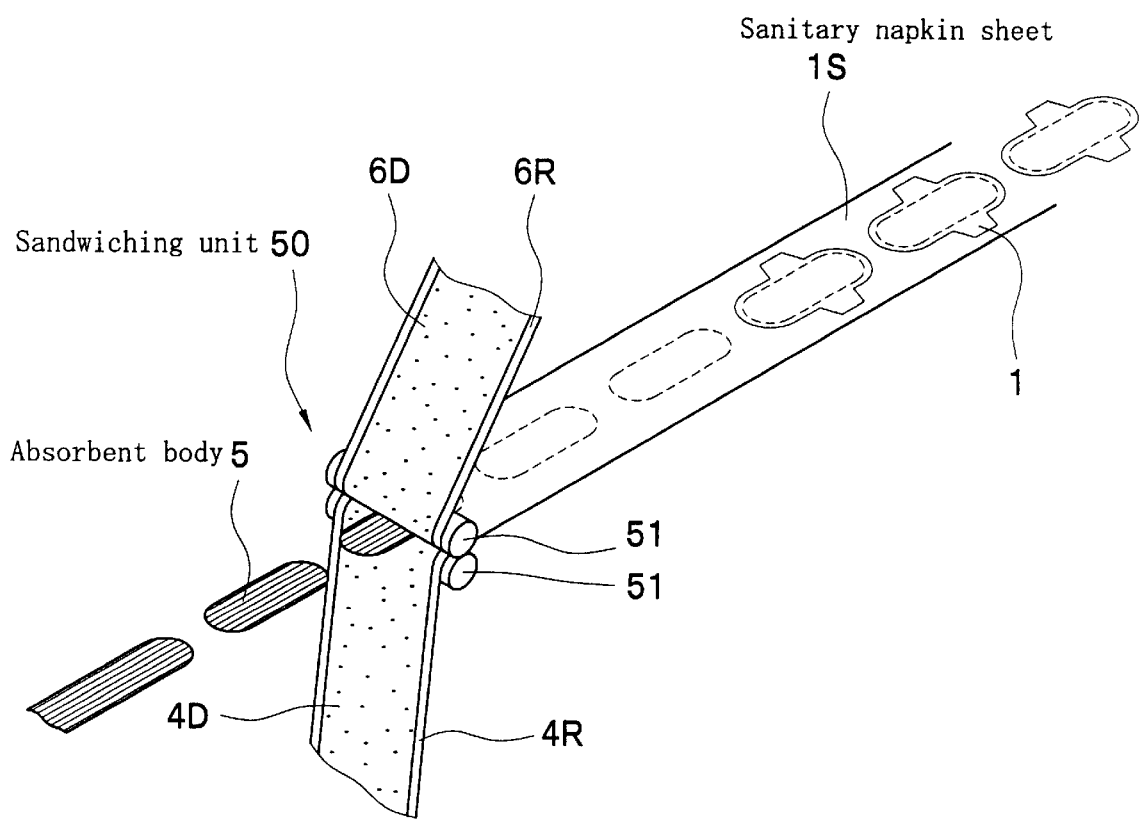

F I G. 6
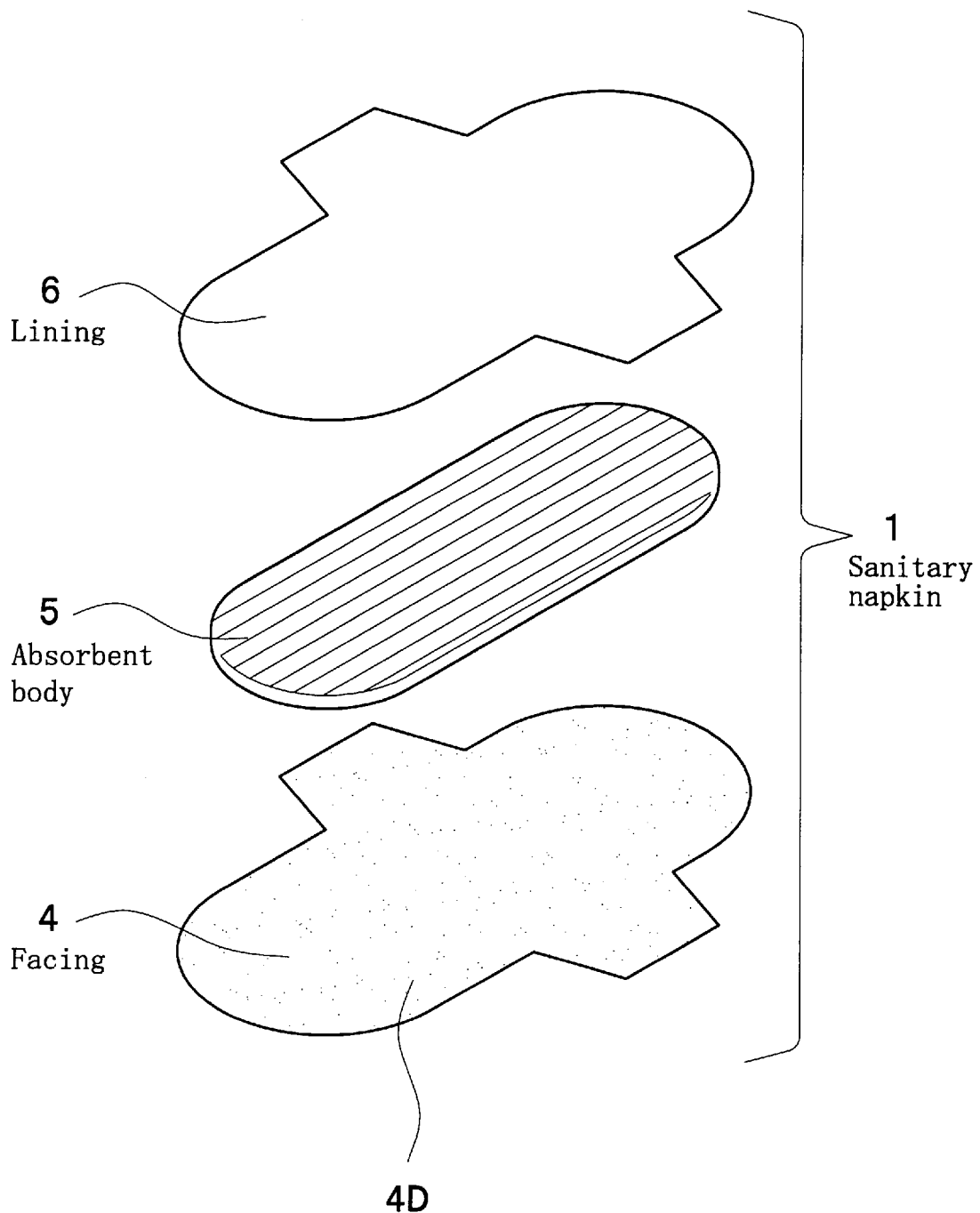

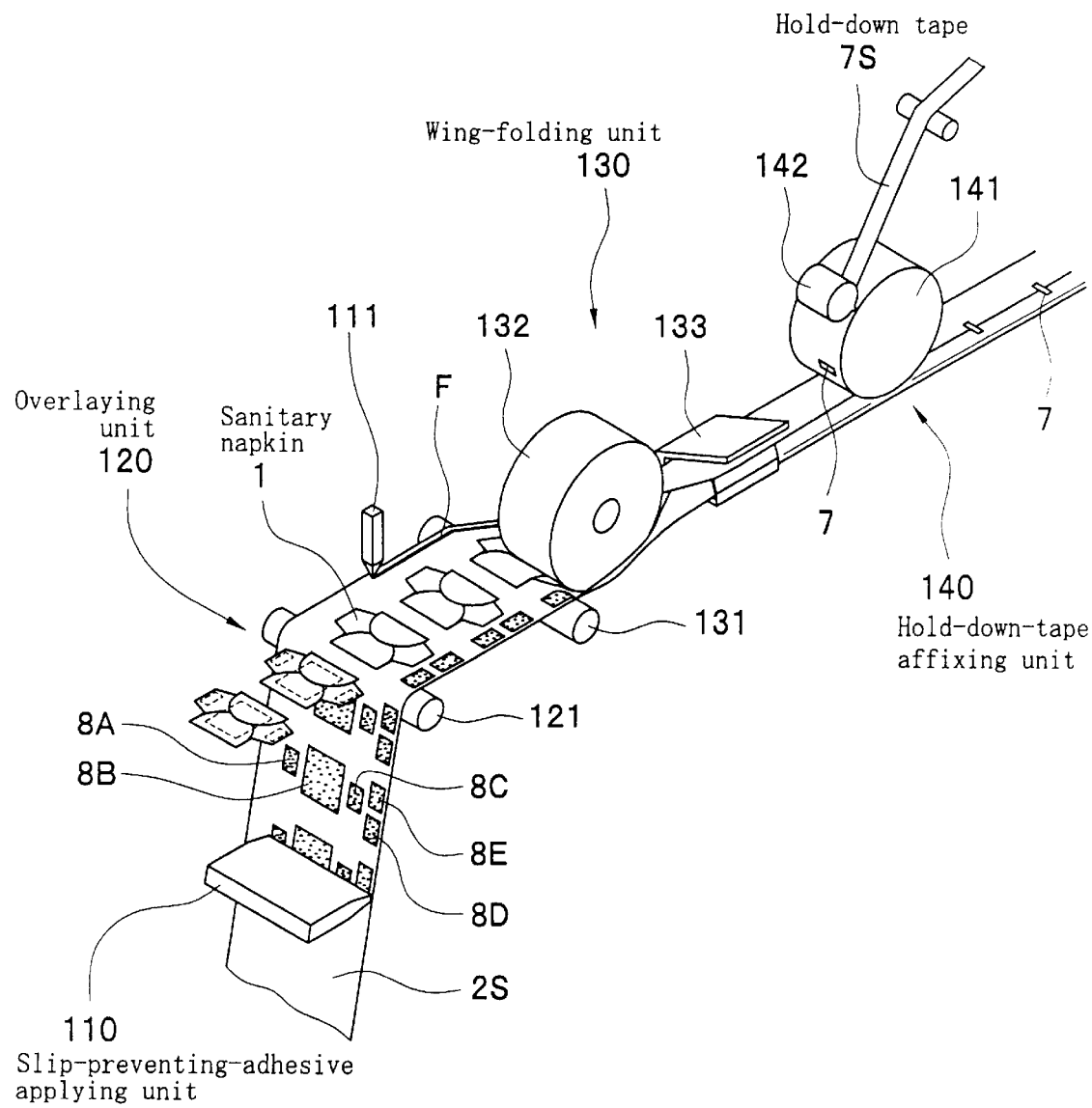
F I G. 7

Sanitary napkin 1

(A)

Wrapping film sheet (B)

MANUFACUTURING EQUIPMENT FOR SANITARY NAPKINS WITH WINGS HAVING NO PEELING-OFF PAPER STRIPS

BACKGROUND OF THE INVENTION

The present invention relates to a sanitary napkin product and its manufacturing equipment.

FIG. 13 (I) is a plan view of a conventional sanitary napkin product 201; FIG. 13 (II), a plan view of the same of which the wrapping film 2 is open. FIG. 14 is an exploded view of the sanitary napkin product 201.

As shown in FIGS. 13 and 14, the conventional sanitary napkin product 201 consists essentially of a wrapping film 2, a peeling-off paper strip 3A, a sanitary napkin 1, and peeling-off paper strips 3B and 3C, each put on another in the order of the description, the sanitary napkin 1 wrapped in the wrapping film 2.

The numeral 7 indicates a hold-down tape strip.

FIG. 15 shows the back of the conventional sanitary napkin 1. As shown in FIG. 15, a wing is formed on each side of the body of the sanitary napkin 1. The leakage of a sanitary napkin with wings is smaller than that of a sanitary napkin without wing. Therefore, consumers prefer sanitary napkins with wings.

On the back of the sanitary napkin 1, adhesive 8a is applied to the center portion extending in the direction of length of the sanitary napkin 1, and adhesive 8b and 8b is applied to both the right and left wings. The adhesive 8a, 8b and 8b adheres to underwear to prevent the slip of the sanitary napkin 1 while it is used.

As shown in FIG. 14, adhesive 2a and 2a is applied to the center portions of the inside of the wrapping film 2. The adhesive 2a and 2a of the wrapping film 2 is overlaid with the peeling-off paper strip 3A. Namely, the peeling-off paper strip 3A is affixed to the wrapping film 2. Then, the sanitary napkin 1 with its wings folded is put on the peeling-off paper strip 3A. The peeling-off paper strip 3A prevents the sanitary napkin 1 from sticking to the wrapping film 2 and thereby reserves the adhesion of the adhesive 8a.

The peeling-off paper strip 3B is inserted between the right and left wings, both folded and overlapping each other, of the sanitary napkin 1 to preserve the adhesion of the adhesive 8b of the wing positioned under the other. The adhesive 8b of the wing positioned on the other is overlaid with the peeling-off paper 3C, which prevents the sanitary napkin 1 from sticking to the wrapping film 2 and thereby preserves the adhesion of the adhesive 8b.

The wrapping film 2 together with the sanitary napkin 1 is folded in three along the dot-dash lines shown in FIG. 13 (II), each of the upper and lower hems of the wrapping film 2 making three layers of itself. Then, as shown in FIG. 13 (I), the upper and lower hems are heat-sealed and the hold-down tape strip 7 is affixed to the wrapping film 2 to produce the sanitary napkin product 201, the wrapping film 2 constituting the wrapper of the sanitary napkin 1.

To use the sanitary napkin 1 wrapped in the wrapping film 2, the hold-down tape strip 7 is removed, the wrapping film 2 of the sanitary napkin product 201 is opened, and the sanitary napkin 1 is peeled off the peeling-off paper strip 3A on the wrapping film 2. Then, the peeling-off paper strips 3C and 3B are peeled off the adhesive 8b and 8b. As mentioned earlier, the adhesion of the adhesive 8a, 8b and 8b of the sanitary napkin 1 is preserved. Therefore, the adhesive 8a, 8b and 8b prevent the sanitary napkin 1 from slipping while it is used.

In case of the conventional sanitary napkin product 201, the peeling-off paper strips 3A, 3B and 3C are necessary to preserve the adhesion of the adhesive 8a, 8b and 8b until the sanitary napkin 1 is used. However, when the sanitary napkin 1 is used, the peeling-off paper strips 3A, 3B and 3C as well as the wrapping film 2 are junked. Using the peeling-off paper strips 3A, 3B and 3C in the sanitary napkin product 201 increases the quantity of wastes and the material cost of the sanitary napkin product 201.

Besides, devices to overlay the adhesive 8a, 8b and 8b with the peeling-off paper strips 3A, 3B and 3C are required, which makes the manufacturing equipment of the sanitary napkin product 201 complex and large.

In accordance with the above, an object of the present invention is to provide a sanitary napkin product which requires no peeling-off paper strips, reducing the quantity of wastes and its material cost, and does not slip while it is used. Another object of the present invention is to provide a manufacturing equipment of the sanitary napkin product.

SUMMARY OF THE INVENTION

According to the first aspect of the present invention, there is provided a sanitary napkin product which is a sanitary napkin with wings on both sides of its body wrapped entirely in a wrapping film. The inside of the wrapping film is coated with silicone, and a coat of slip-preventing adhesive which comes easily off silicone coats is formed between the silicone-coated side of the wrapping film and the back of the sanitary napkin.

According to the second aspect of the present invention, there is provided a sanitary napkin product according to the first aspect wherein (i) both the longitudinal end parts of the body of the sanitary napkin are folded onto the front side of the sanitary napkin, (ii) the wings on both sides of the sanitary napkin are folded onto the front side of the sanitary napkin, and (iii) the slip-preventing adhesive is applied to the backs of the middle part and longitudinal end parts of the body, and the backs of the wings, of the sanitary napkin.

According to the third aspect of the present invention, there is provided a sanitary-napkin-product manufacturing equipment which comprises (i) a manufacturing machine to manufacture a sanitary napkin with wings and (ii) a wrapping machine to apply slip-preventing adhesive, which comes easily off silicone coats, to the back of the sanitary napkin and wrap the sanitary napkin in a wrapping film, of which the inside is coated with silicone, to produce a sanitary napkin product.

According to the fourth aspect of the present invention, there is provided a sanitary-napkin-product manufacturing equipment according to the third aspect of which the manufacturing machine, wherein a continuous facing sheet fed from its roll, a continuous absorbent sheet fed from its roll, and a continuous lining sheet fed from its roll run respectively, comprises (i) an absorbent-body cutout unit which cuts out absorbent bodies one after another at intervals in the running direction from the running absorbent sheet, (ii) a lining-sheet-adhesive applying unit which applies adhesive to the running lining sheet continuously in the running direction, (iii) a facing-sheet-adhesive applying unit which applies adhesive to the running facing sheet continuously in the running direction, (iv) a sandwiching unit which puts the absorbent bodies sequentially between the running facing sheet and the running lining sheet and puts them together to make a sanitary napkin sheet, (v) a heat-sealing unit which seals with heat the portion inside and along the outline of the portion including the absorbent body which becomes the sanitary napkin, and (vi) a sanitary-napkin cutout unit which cuts out pieces of the sanitary napkin one after another at intervals from the sanitary napkin sheet holding the absorbent bodies inside.

According to the fifth aspect of the present invention, there is provided a sanitary-napkin-product manufacturing equipment according to the fourth aspect of which the absorbent-body cutout unit comprises paired anvil roller and die-cut roller. The die-cut roller has cutter blades on its periphery to cut out absorbent bodies, and the absorbent sheet runs into between the paired anvil roller and die-cut roller for absorbent bodies to be cut out one after another.

According to the sixth aspect of the present invention, there is provided a sanitary-napkin-product manufacturing equipment according to the fourth or fifth aspect of which the heat-sealing unit comprises paired anvil roller and heat-sealing roller. The heat-sealing roller has nonheating portions on its periphery, each a little smaller than the sanitary napkin, and the sanitary napkin sheet runs into between the paired anvil roller and heat-sealing roller.

According to the seventh aspect of the present invention, there is provided a sanitary-napkin-product manufacturing equipment according to the fourth, or fifth, or sixth aspect of which the sanitary-napkin cutout unit comprises paired anvil roller and die-cut roller. The die-cut roller has cutter blades on its periphery, and the sanitary napkin sheet runs into between the paired anvil roller and die-cut roller for pieces of the sanitary napkin to be cut out one after another.

According to the eighth aspect of the present invention, there is provided a sanitary-napkin-product manufacturing equipment according to the third aspect of which the wrapping machine comprises (i) a longitudinally folding unit which folds both the longitudinal end parts of the body of the sanitary napkin onto the front side of the sanitary napkin, (ii) a slip-preventing-adhesive applying unit, in front of which a continuous wrapping film sheet with one side coated with silicone fed from its roll runs, and which applies slip-preventing adhesive to the silicone-coated side of the wrapping film sheet at intervals in the running direction, (iii) an overlaying unit which puts the sanitary napkin on the slip-preventing adhesive on the running wrapping film sheet, (iv) a wing-folding unit which folds the running wrapping film sheet together with the sanitary napkin in the direction of width of the wrapping film sheet, the sanitary napkin held inside the wrapping film sheet, the wings of the sanitary napkin folded, (v) a hold-down-tape affixing unit which cuts a continuous hold-down tape fed from its roll into hold-down tape strips and affixes them at intervals in the running direction onto both the hems overlapping each other of the wrapping film sheet, (vi) a film-sealing unit which seals with heat the intermediate portions between pieces of the sanitary napkin at intervals in the running direction, and (vii) a cutting unit which cuts off the wrapping film sheet in the intermediate portions between pieces of the sanitary napkin.

According to the ninth aspect of the present invention, there is provided a sanitary-napkin-product manufacturing equipment according to the eighth aspect wherein (i) the slip-preventing-adhesive applying unit applies slip-preventing adhesive to such parts of the silicone-coated side of the running wrapping film sheet as correspond positionally to the middle part and longitudinal end parts of the body, and both the wings, of the sanitary napkin and (ii) the overlaying unit puts the sanitary napkin with its longitudinal end parts folded on the slip-preventing adhesive on the wrapping film sheet, the back of the sanitary napkin coming into contact with the slip-preventing adhesive, and the middle part of the body and the wings of the sanitary napkin corresponding positionally to the slip-preventing-adhesive-applied counterparts of the wrapping film sheet.

According to the tenth aspect of the present invention, there is provided a sanitary-napkin-product manufacturing equipment according to the eighth or ninth aspect of which the wing-folding unit comprises (i) a feed roller which is set freely rotatably in a vertical plane, (ii) a holding-down roller which is narrower than the wrapping film sheet, positioned lower than the feed roller, and set freely rotatably, and (iii) a folder. The wrapping film sheet runs on the feed roller, under the holding-down roller, and through the folder to be folded widthwise continuously, the longitudinal end parts of the body of the sanitary napkin overlaid with the slip-preventing-adhesive-applied counterparts of the wrapping film sheet.

According to the eleventh aspect of the present invention, there is provided a sanitary-napkin-product manufacturing equipment according to eighth, or ninth, or tenth aspect of which the hold-down-tape affixing unit comprises (i) a hold-down-tape cutting subunit which cuts the hold-down tape into hold-down tape strips one after another, and (ii) an affixing roller which affixes the hold-down tape strips to the hems of the running wrapping film sheet.

In the present invention, the concept of sanitary napkin product includes pantie liner product, menstrual napkin product, maternity napkin product, and incontinent pad product at the least, and the concept of sanitary napkin includes pantie liner, menstrual napkin, maternity napkin, and incontinent pad at the least.

The advantages offered by the first aspect of the present invention are mainly as follows. The slip-preventing adhesive comes easily, without deterioration, off the silicone-coated surface of the wrapping film to stay on the back of the sanitary napkin. Accordingly, the positional slippage of the sanitary napkin can be prevented while it is used. Besides, no peeling-off paper is required, which reduces the quantity of wastes and the material cost of the sanitary napkin product.

The advantages offered by the second aspect of the present invention are mainly as follows. The slip-preventing adhesive comes easily, without deterioration, off the silicone-coated surface of the wrapping film to stay on the back of the sanitary napkin. Accordingly, the positional slippage of the sanitary napkin can be prevented while it is used. Besides, no peeling-off paper is required, which reduces the quantity of wastes and the material cost of the sanitary napkin product. Moreover, because slip-preventing adhesive can be applied to only the necessary parts, the material cost further decreases.

The advantages offered by the third aspect of the present invention are mainly as follows. The slip-preventing adhesive comes easily, without deterioration, off the silicone-coated surface of the wrapping film to stay on the back of the sanitary napkin. Accordingly, the positional slippage of the sanitary napkin can be prevented while it is used. Besides, because no peeling-off paper is required, the quantity of wastes and the material cost of the sanitary napkin product are reduced.

The advantages offered by the fourth aspect of the present invention are mainly as follows. While a continuous facing sheet, a continuous absorbent sheet, and a continuous lining sheet fed from their rolls, respectively, are running, absorbent bodies are cut out sequentially at intervals in the running direction from the running absorbent sheet by the absorbent-body cutout unit, and the facing and lining sheets are coated continuously in the running direction with adhesive by the facing-sheet-adhesive and lining-sheet-adhesive applying units, respectively. The running facing and lining sheets are put together by the sandwiching unit, absorbent bodies held between them, the sheets and bodies constituting a sanitary napkin sheet. By the heat-sealing unit, the running sanitary napkin sheet is heat-sealed at the portion inside and along the outline of the portion including the absorbent body which becomes the sanitary napkin. Then, pieces of the sanitary napkin are cut out at intervals in the running direction from the running sanitary napkin sheet. Thus, a sanitary napkin product can be produced which does not slip while it is used and does not require any peeling-off paper strips, reducing the quantity of wastes and its material cost.

The advantage offered by the fifth aspect of the present invention is that absorbent bodies can be cut out from a running absorbent sheet sequentially.

The advantage offered by the sixth aspect of the present invention is that the area of a running sanitary napkin sheet around its absorbent bodies can be heat-sealed continuously without deteriorating the absorbent bodies.

The advantage offered by the seventh aspect of the present invention is that pieces of a sanitary napkin can be cut out one after another from a running sanitary napkin sheet.

The advantages offered by the eighth aspect of the present invention are mainly as follows. Both the longitudinal end parts of the body of a sanitary napkin are folded onto the front by the longitudinally folding unit. On the other hand, a continuous wrapping film sheet fed from its roll and running is coated at intervals in its running direction with slip-preventing adhesive by the slip-preventing-adhesive applying unit. Pieces of the sanitary napkin are put on the slip-preventing adhesive on the running wrapping film sheet by the overlaying unit. The running wrapping film sheet, together with the sanitary napkin, is folded in the direction of width of the wrapping film sheet by the wing-folding unit, the sanitary napkin inside the wrapping film sheet, both the wings of the sanitary napkin folded. In the hold-down tape affixing unit, a continuous hold-down tape fed from its roll is cut into hold-down tape strips, which are affixed, at intervals in the running direction of the wrapping film sheet, to both the hems overlapping each other of the wrapping film sheet. The wrapping film sheet is heat-sealed, at intervals, in the intermediate portions between pieces of the sanitary napkin by the film-sealing unit. Lastly, the wrapping film sheet is cut off in the intermediate portions between pieces of the sanitary napkin by the cutting unit to produce pieces of a sanitary napkin product. Thus, a sanitary napkin product can be produced which does not slip while it is used and does not require any peeling-off paper strips, reducing the quantity of wastes and its material cost.

The advantage offered by the ninth aspect of the present invention is as follows. Slip-preventing adhesive is applied to such parts of the silicone-coated side of a wrapping film sheet by the slip-preventing-adhesive applying unit as correspond positionally to the middle part and both the longitudinal end parts of the body, and both the wings, of a sanitary napkin. In the overlaying unit, the sanitary napkin with its wings folded is put on the slip-preventing adhesive on the wrapping film sheet, the back of the sanitary napkin coming into contact with the slip-preventing adhesive, the middle part of the body and the wings of the sanitary napkin corresponding positionally to their slip-preventing-adhesive-applied counterparts. Thus, a coat of slip-preventing adhesive can be formed between the back of the sanitary napkin with its wings folded and the silicone-coated side of the wrapping film sheet.

The advantage offered by the tenth aspect of the present invention is as follows. A running wrapping film sheet is pushed down together with the sanitary napkin by the holding-down roller to be given a U shape as seen in its running direction. Both the wings of the U consisting of the wrapping film sheet and the sanitary napkin are folded down by the folder. Thus, slip-preventing-adhesive-applied parts of the wrapping film sheet corresponding positionally to the longitudinal end parts of the body of the sanitary napkin are put on the latter.

The advantage offered by the eleventh aspect of the present invention is that a running hold-down tape is cut into hold-down tape strips by the hold-down-tape cutting subunit, which are affixed one after another by the affixing roller to the hems of the wrapping film sheet at intervals in the running direction of the wrapping film sheet.

BRIEF DESCRIPTION OF THE DRAWINGS

The features and advantages of the present invention will become more clearly appreciated from the following description in conjunction with the accompanying drawings, in which:

FIG. 4 is a schematic perspective view of the sandwiching unit of the manufacturing machine;

FIG. 6 is an exploded view of the sanitary napkin;

FIG. 7 is a schematic perspective view of the wrapping machine;

FIG. 9 (B), the subsequent state;

FIG. 11 (II), a schematic perspective view of the same of which the wrapping film is open;

FIG. 13 (II), a schematic plan view of the same of which the wrapping film is open;

DETAILED DESCRIPTION OF THE PREFERRED EMBODIMENTS

With reference to the drawings, a preferred embodiment of the present invention will now be described.

Figure 1:
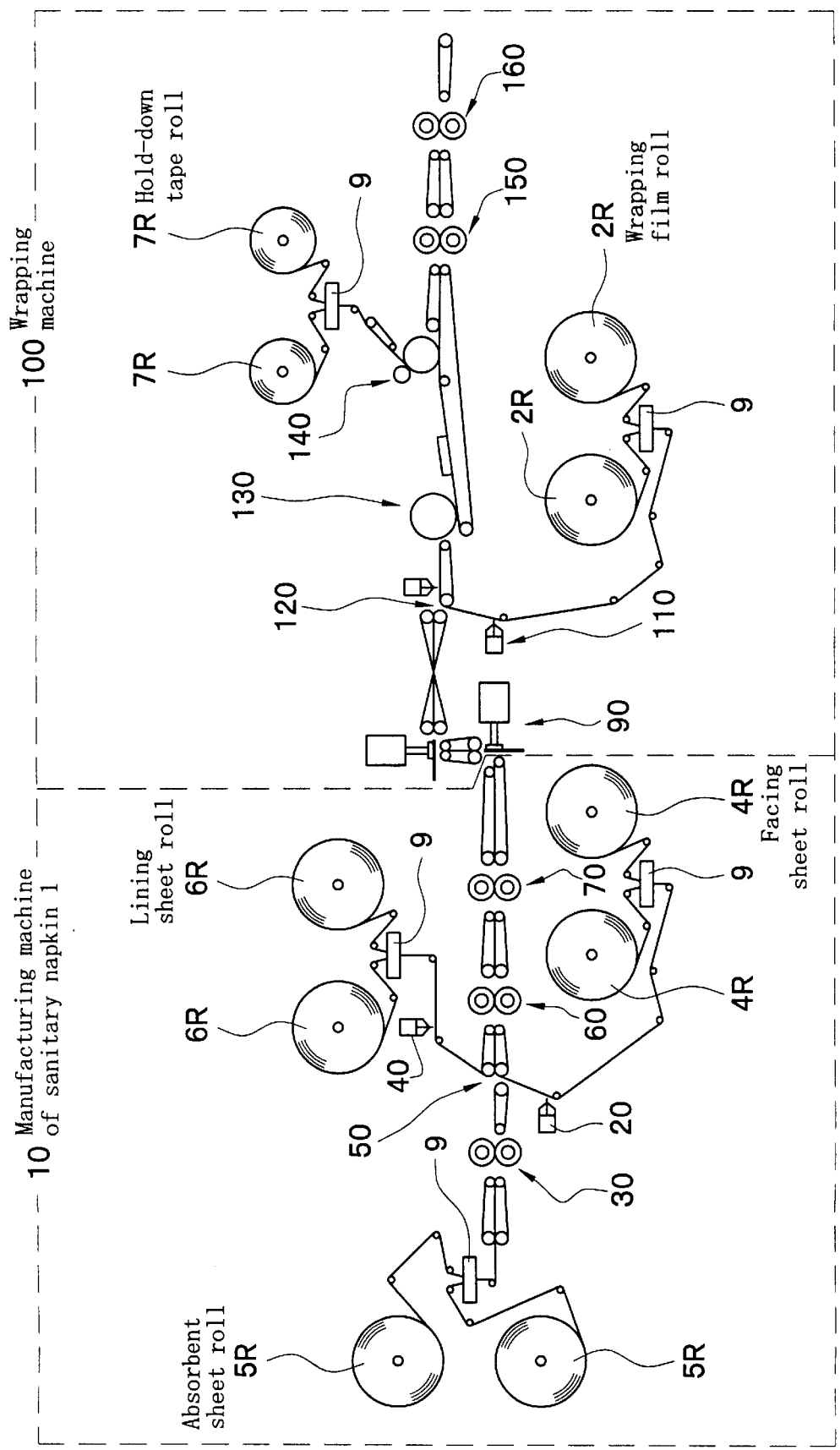
FIG. 1 is a schematic side view of an embodiment of manufacturing equipment of one form of sanitary napkin product of the present invention.

FIG. 1 is a schematic side view of an embodiment of manufacturing equipment of one form of sanitary napkin product of the present invention. As shown in FIG. 1, the manufacturing equipment of the sanitary napkin product comprises a manufacturing machine 10 (the left hand side in FIG. 1) which manufactures the sanitary napkin such as pantie liner, menstrual napkin, maternity napkin, and incontinent pad and a wrapping machine 100 (the right hand side in FIG. 1) which wraps the sanitary napkin manufactured by the manufacturing machine 10 to produce the sanitary napkin product, the two machines connected in series.

The manufacturing machine 10 of the sanitary napkin will first be described. The manufacturing machine 10 of the sanitary napkin, indicated by the numeral "1" in the relevant drawings, comprises a facing-sheet-adhesive applying unit 20, an absorbent-body cutout unit 30, a lining-sheet-adhesive applying unit 40, a sandwiching unit 50, a heat-sealing unit 60, and a sanitary-napkin cutout unit 70.

Figure 2:
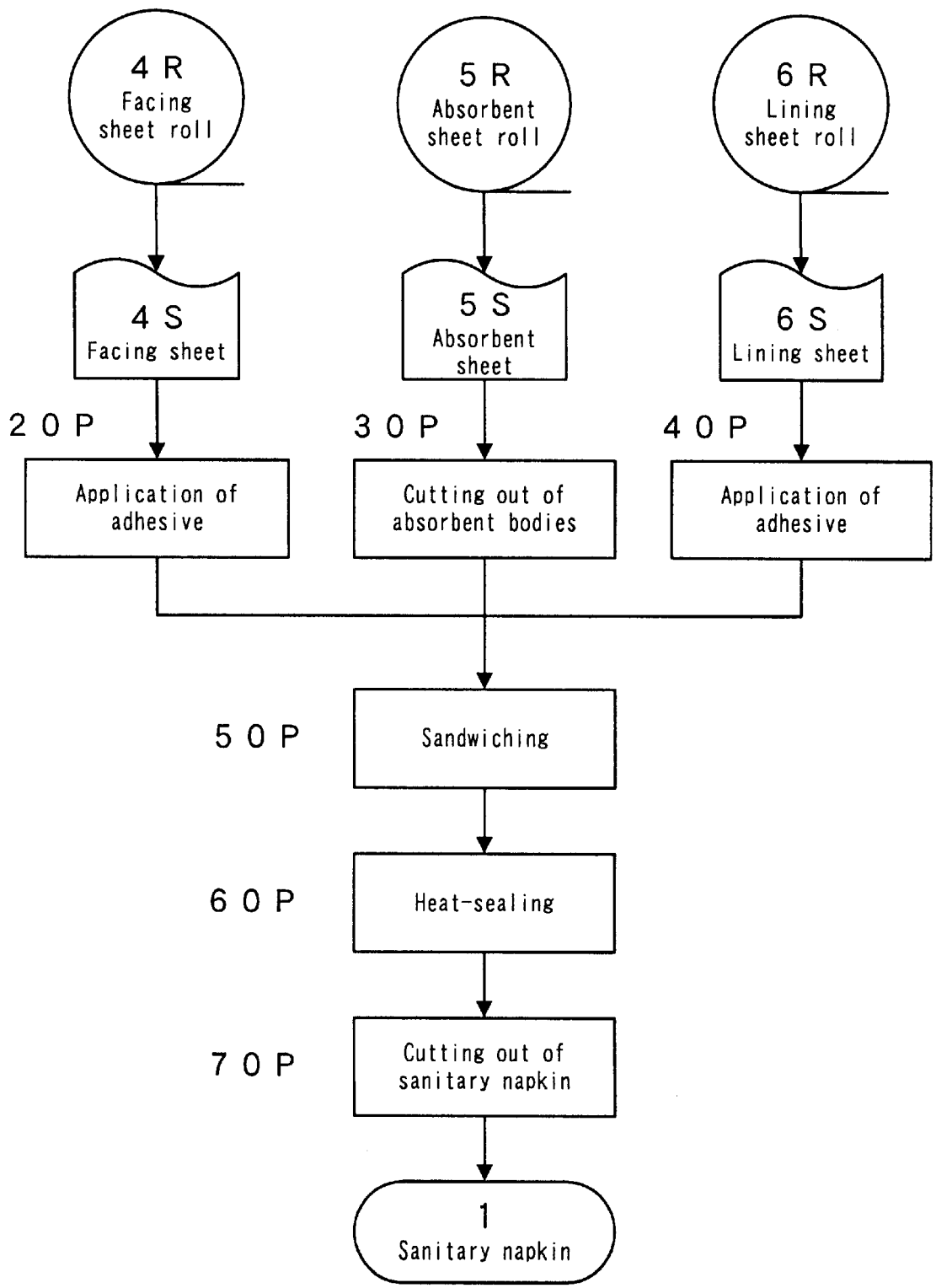
FIG. 2 is a flowchart showing the manufacturing process of the sanitary napkin by the manufacturing machine of the manufacturing equipment of FIG. 1.

FIG. 2 is a flowchart showing the manufacturing process of the sanitary napkin 1 by the manufacturing machine 10. The signs 20P–70P indicate the subprocesses of the units 20–70 of the manufacturing machine 10.

The signs 4R and 4R indicate facing sheet rolls; the signs 5R and 5R, absorbent sheet rolls; the signs 6R and 6R, lining sheet rolls. Two rolls are provided for each of the facing sheet 4S, absorbent sheet 5S, and lining sheet 6S so that each sheet can be fed by either roll through a corresponding connecting device 9 without interruption.

Each facing sheet roll 4R consists of a facing sheet 4S. The facing sheet 4S is of mesh film or nonwoven fabric.

Each absorbent sheet roll 5R consists of an absorbent sheet 5S. The absorbent sheet 5S is of dry-pulp nonwoven fabric containing polymer absorbent, or of dry-pulp nonwoven fabric overlaid with tissue paper.

Each lining sheet roll 6R consists of a lining sheet 6S. The lining sheet 6S is a film of synthetic resin.

The units 20–70 of the manufacturing machine 10 will now be described in detail.

The absorbent-body cutout unit 30 will be described first.

Figure 3:
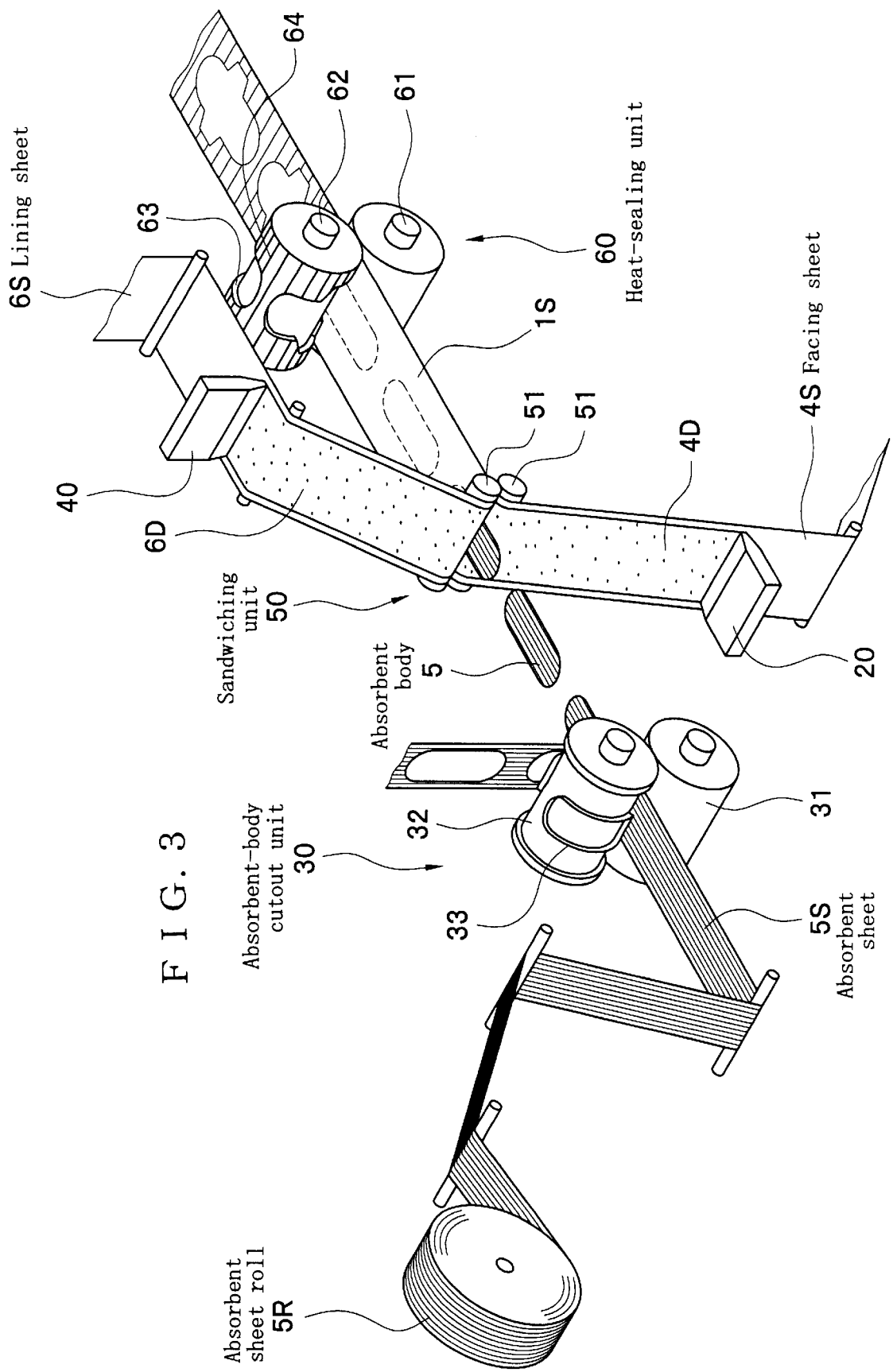
FIG. 3 is a schematic perspective view of the facing-sheet-adhesive applying unit, absorbent-body cutout unit, lining-sheet-adhesive applying unit, sandwiching unit, and heat-sealing unit of the manufacturing machine.

FIG. 3 is a schematic perspective view of the facing-sheet-adhesive applying unit 20, absorbent-body cutout unit 30, lining-sheet-adhesive applying unit 40, sandwiching unit 50, and heat-sealing unit 60. As shown in FIG. 3, the absorbent-body cutout unit 30 comprises paired, freely rotatable anvil roller 31 and die-cut roller 32.

Cutter blades 33 are formed on the periphery of the die-cut roller 32 at intervals in the direction of rotation of the die-cut roller 32.

Although two cutter blades 33 are formed on the die-cut roller 32 in FIG. 3, any number of cutter blades 33 without particular limitation may be formed.

Besides, although in FIG. 3 each cutter blade 33 is formed in a rectangular shape, of which the long sides are in the direction of rotation of the die-cut roller 32, and of which the short sides are rounded, it can dispense with the long-side portions, consisting of only the short-side portions in a circular arc shape.

Moreover, cutter blades 33 may be formed in multiple rows in the direction of rotation of the die-cut roller 32 on the periphery of the die-cut roller 32. As the number of rows increases, the production quantity of the sanitary napkin 1 per unit time increases. Therefore, multiple-row arrangement of cutter blades 33 is preferable. The width of the die-cut roller 32 can be determined in accordance with the width of the absorbent sheet 5S. In case that the number of rows of cutter blades 33 is large, the absorbent sheet 5S will be widened. In case that the number of rows of cutter blades 33 is small, the absorbent sheet 5S will be narrowed.

The absorbent sheet 5S fed from an absorbent sheet roll 5R runs into between the paired anvil roller 31 and die-cut roller 32 of the absorbent-body cutout unit 30. The absorbent sheet 5S is running, and the paired anvil roller 31 and die-cut roller 32 are rotating synchronously with the running speed of the absorbent sheet 5S. Accordingly, each time a cutter blade 33 of the die-cut roller 32 meets the periphery of the anvil roller 31, an absorbent body 5 is cut out from the absorbent sheet 5S (30P). Absorbent bodies 5 thus cut out are fed to the sandwiching unit 50, which will be described later.

Figure 12:
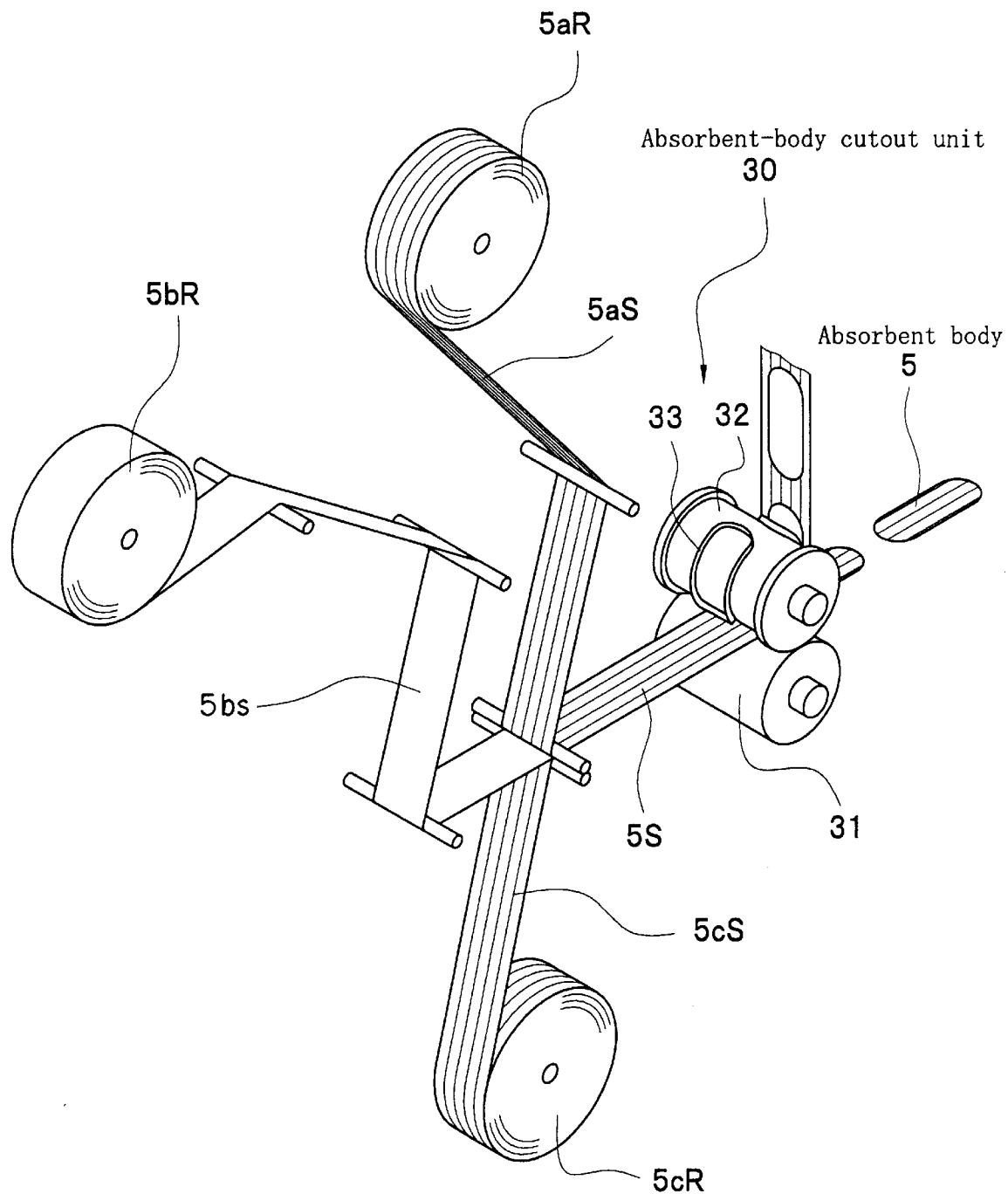
FIG. 12 is a schematic perspective view of a means to manufacture another type of absorbent body of the present invention.

Alternatively, as shown in FIG. 12, sheets 5aS, 5bS and 5cS may be fed from sheet rolls 5aR, 5bR and 5cR and put together in layers to constitute an absorbent sheet 5S. These sheets 5aS, 5bS and 5cS constitute an equivalent for the "absorbent sheet" mentioned in claims of the present invention.

The facing-sheet-adhesive applying unit 20 will next be described.

The facing-sheet-adhesive applying unit 20 is a known nozzle. The facing-sheet-adhesive applying unit 20 is to apply adhesive 4D to the facing sheet 4S. Adhesive 4D can be applied continuously to the running facing sheet 4S by the facing-sheet-adhesive applying unit 20 (20P).

Any adhesives such as hot melt adhesive, without particular limitation, can be used as the adhesive 4D. Besides, although the facing-sheet-adhesive applying unit 20 is shown as a nozzle in FIG. 3, it may be a transfer roller.

The lining-sheet-adhesive applying unit 40 will next be described.

As in the case of the facing-sheet-adhesive applying unit 20, the lining-sheet-adhesive applying unit 40 is a known nozzle. The lining-sheet-adhesive applying unit 40 is to apply adhesive 6D to the lining sheet 6S. Adhesive 6D can be applied continuously to the running lining sheet 6S by the lining-sheet-adhesive applying unit 40 (40P).

Any adhesives such as hot melt adhesive, without particular limitation, can be used as the adhesive 6D. Besides, although the lining-sheet-adhesive applying unit 40 is shown as a nozzle in FIG. 3, it may be a transfer roller.

The sandwiching unit 50 will next be described.

FIG. 4 is a schematic perspective view of the sandwiching unit 50. As shown in FIGS. 3 and 4, the sandwiching unit 50 comprises a pair of rollers 51 and 51. The facing and lining sheets 4S and 6S holding absorbent bodies 5 between them run into between the paired rollers 51 and 51. Then, the facing and lining sheets 4S and 6S are pressed by the paired rollers 51 and 51 and stick to each other, absorbent bodies 5 held between them (50P).

The facing and lining sheets 4S and 6S holding absorbent bodies 5 between them will hereinafter be referred to as sanitary napkin sheet 1S.

The heat-sealing unit 60 will next be described.

As shown in FIG. 3, the heat-sealing unit 60 comprises paired anvil roller 61 and heat-sealing roller 62.

The heat-sealing roller 62 has a built-in heat source, which raises the temperature of the periphery of the heat-sealing roller 62. Nonheating portions 63 are formed in the periphery of the heat-sealing roller 62. Each nonheating portion 63 is a recess, which is larger than the absorbent body 5 and given the shape of the winged sanitary napkin 1 so that the absorbent body 5 does not deteriorate from heat.

The non-recessed portion of the periphery of the heat-sealing roller 62 constitutes a heating portion 64.

The anvil roller 61 may also have a built-in heat source so that the heat-sealing temperature can be adjusted to heat-seal sanitary napkin sheets 1S of various materials.

The width of the anvil roller 61 and heat-sealing roller 62 can be determined in accordance with the width of the sanitary napkin sheet 1S.

The sanitary napkin sheet 1S runs into between the anvil roller 61 and the heat-sealing roller 62 of the heat-sealing unit 60. The sanitary napkin sheet 1S is running, and the anvil roller 61 and heat-sealing roller 62 are rotating synchronously with the running speed of the sanitary napkin sheet 1S. Accordingly, the area around each absorbent body 5 of the sanitary napkin sheet 1S (the hatched area shown in FIG. 3) is caught between the anvil roller 61 and the heating portion 64 of the heat-sealing roller 62 and heat-sealed. On the other hand, each absorbent body 5 is accommodated in a nonheating portion 63 and, accordingly, does not deteriorate from heat. Thus, the heat-sealing unit 60 heat-seals the sanitary napkin sheet 1S continuously without deteriorating absorbent bodies 5 (60P).

In FIG. 3, the hatched area of the sanitary napkin sheet 1S is heat-sealed, and the non-hatched portions are not heat-sealed.

The sanitary-napkin cutout unit 70 will next be described.

Figure 5:
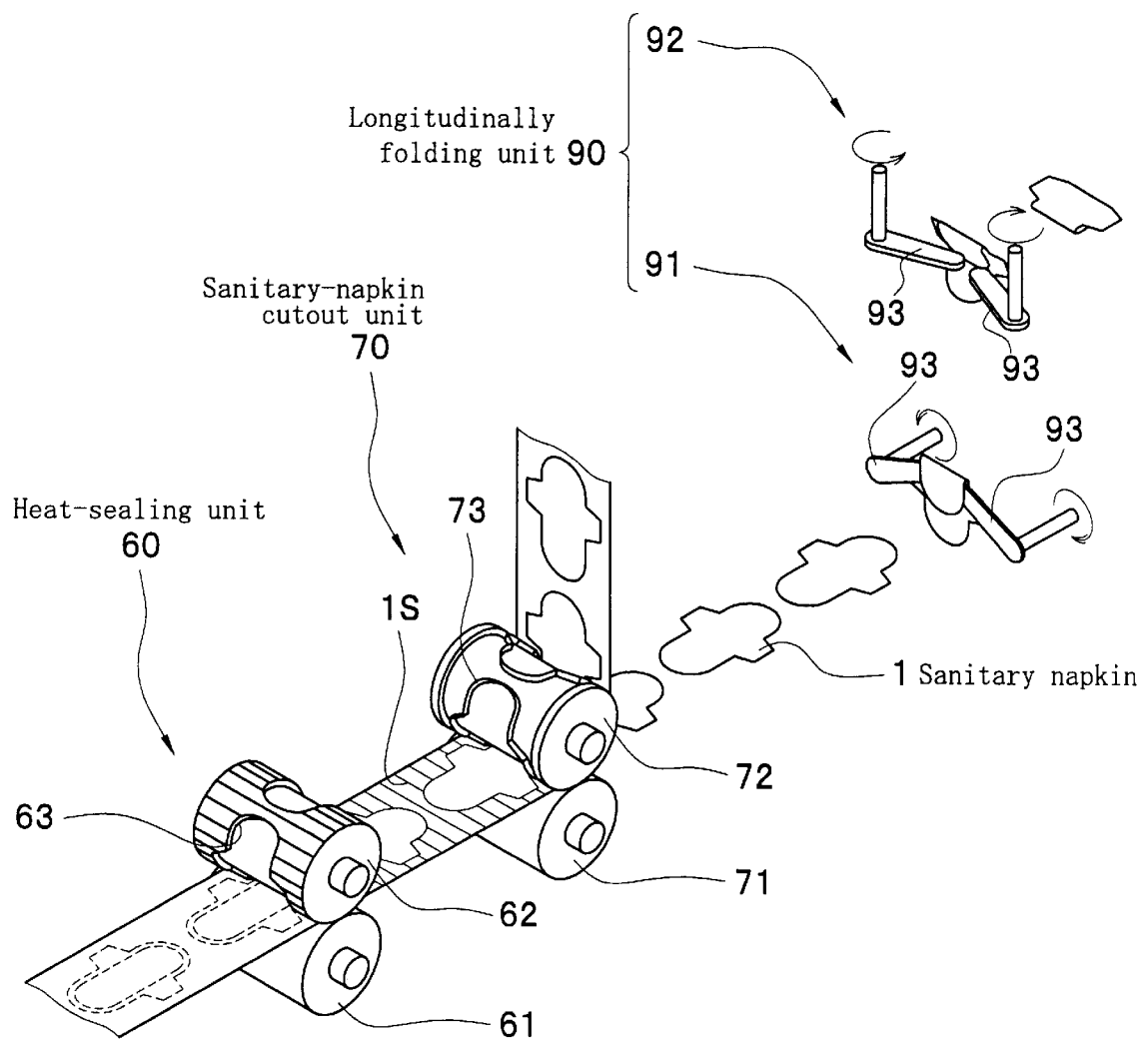
FIG. 5 is a schematic perspective view of the heat-sealing unit and sanitary-napkin cutout unit of the manufacturing machine, and the longitudinally folding unit of the wrapping machine of the manufacturing equipment of FIG. 1.

FIG. 5 is a schematic perspective view of the heat-sealing unit 60 and the sanitary-napkin cutout unit 70, and the longitudinally folding unit 90 of the wrapping machine 100. As shown in FIG. 5, the sanitary-napkin cutout unit 70 comprises paired anvil roller 71 and die-cut roller 72. Formed on the periphery of the die-cut roller 72 are cutter blades 73 in the shape of the winged sanitary napkin 1 and in a size larger than that of the nonheating portions 63 of the heat-sealing roller 62 of the heat-sealing unit 60.

The width of the anvil roller 71 and die-cut roller 72 can be determined in accordance with the width of the sanitary napkin sheet 1S.

The sanitary napkin sheet 1S runs into between the paired anvil roller 71 and die-cut roller 72 of the sanitary-napkin cutout unit 70. The sanitary napkin sheet 1S is running, and the paired anvil roller 71 and die-cut roller 72 are rotating synchronously with the running speed of the sanitary napkin sheet 1S. Accordingly, each time a cutter blade 73 of the die-cut roller 72 meets the periphery of the anvil roller 71, a piece of the sanitary napkin 1 is cut out from the sanitary napkin sheet 1S (70P). Pieces of the sanitary napkin 1 thus cut out are fed to the longitudinally folding unit 90 of the wrapping machine 100.

The sanitary napkin sheet 1S, after the sanitary napkin 1 is cutout from it, is wound up (not shown) and disposed of.

The manufacturing machine 10 of the sanitary napkin 1 with the above construction manufactures the sanitary napkin 1 as follows.

As shown in FIGS. 2 and 3, the absorbent sheet 5S from an absorbent sheet roll 5R is fed into between the anvil roller 31 and die-cut roller 32 of the absorbent-body cutout unit 30, and absorbent bodies 5 are cut out one after another from the absorbent sheet 5S (30P).

On the other hand, the facing sheet 4S from a facing sheet roll 4R is fed to the facing-sheet-adhesive applying unit 20, where adhesive 4D is applied to the facing sheet 4S (20P).

The lining sheet 6S from a lining sheet roll 6R is fed to the lining-sheet-adhesive applying unit 40, where adhesive 6D is applied to the lining sheet 6S (40P).

The facing-sheet 4S and the lining sheet 6S holding absorbent bodies 5 between them are fed to the sandwiching unit 50 and caught and pressed between the paired rollers 51 and 51 to become an sanitary napkin sheet 1S (50P).

The sanitary napkin sheet 1S is fed into between the anvil roller 61 and the heat-sealing roller 62 of the heat-sealing unit 60. The area around each absorbent body 5 of the sanitary napkin sheet 1S is caught between the anvil roller 61 and the heating portion 64 of the heat-sealing roller 62 and heat-sealed. On the other hand, each absorbent body 5 is accommodated in a nonheating portion 63 of the heat-sealing roller 62 and, accordingly, does not deteriorate from heat. Thus, the sanitary napkin sheet 1S can be heat-sealed continuously, without deteriorating absorbent bodies 5, by the heat-sealing unit 60 (60P).

As shown in FIG. 5, the sanitary napkin sheet 1S is fed into between the anvil roller 71 and die-cut roller 72 of the sanitary-napkin cutout unit 70, where each time a cutter blade 73 of the die-cut roller 72 meets the periphery of the anvil roller 71, a piece of sanitary napkin 1 is cut out from the sanitary napkin sheet 1S (70P).

FIG. 6 is an exploded view of the sanitary napkin 1.

Figure 13:
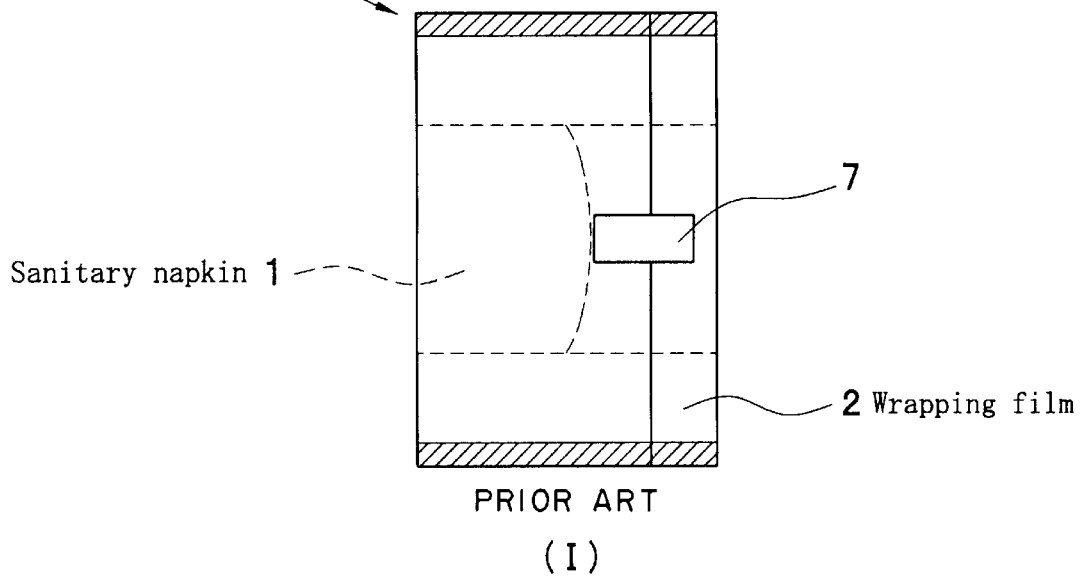
FIG. 13 (I) is a schematic plan view of a conventional sanitary napkin product.
Figure 13:
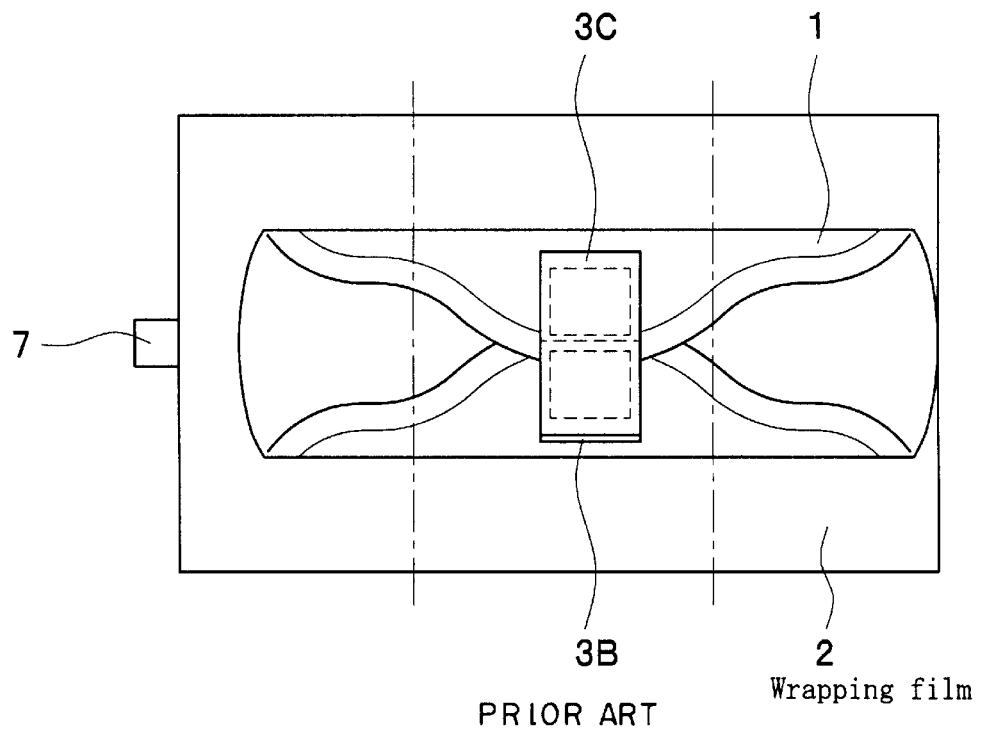
Figure 14:
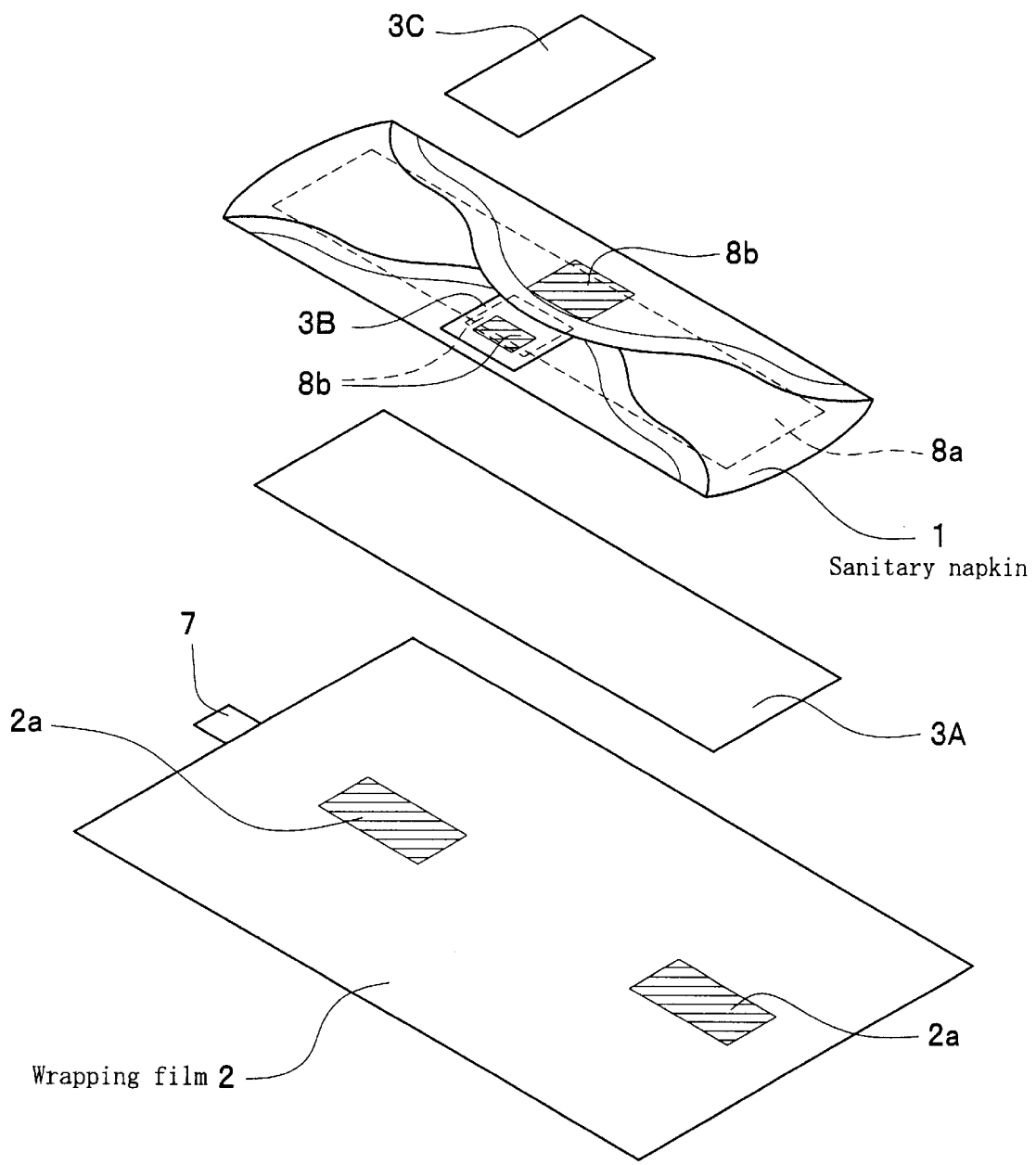
FIG. 14 is an exploded view of the conventional sanitary napkin product.
Figure 15:
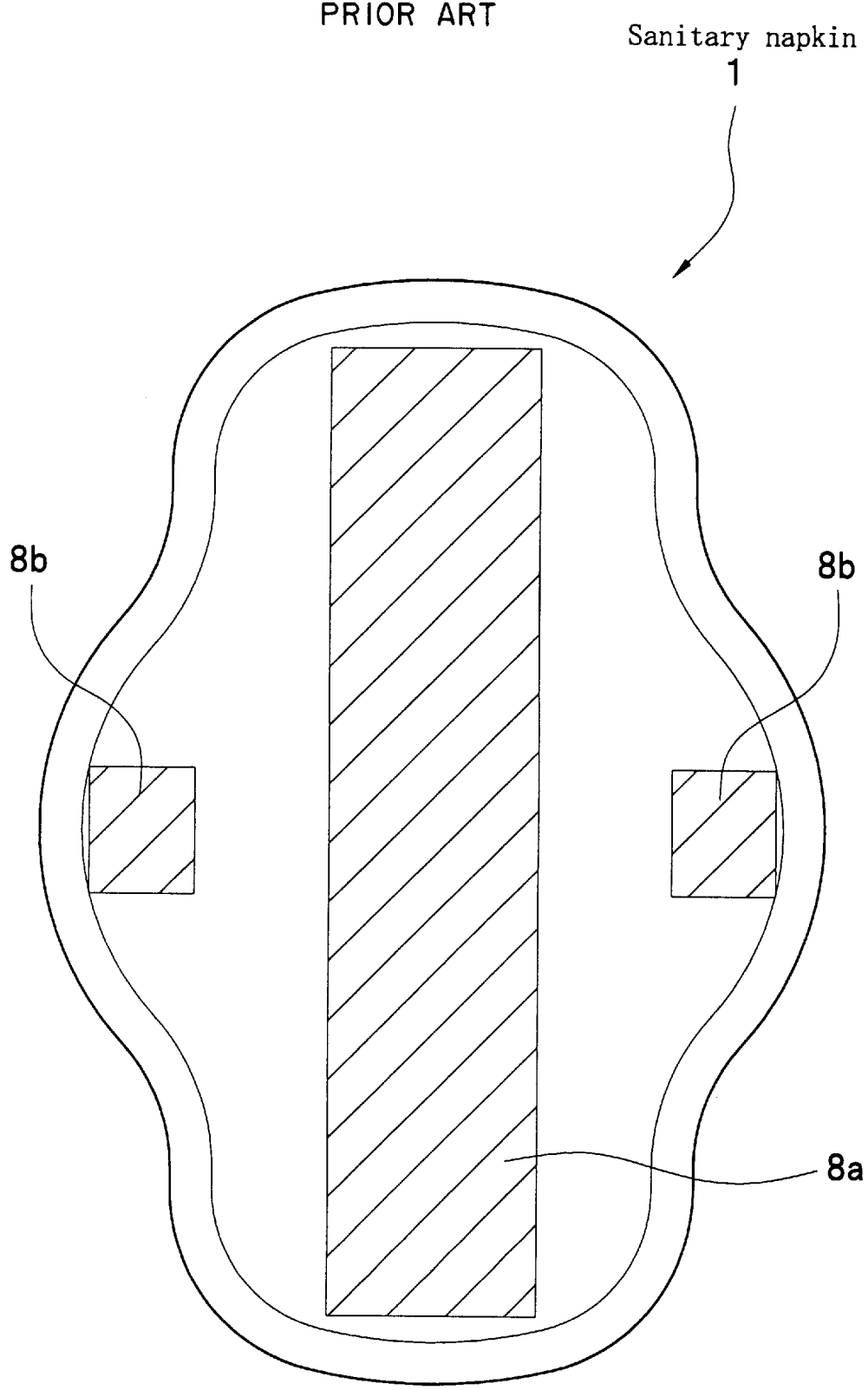
FIG. 15 shows the back of the conventional sanitary napkin.

As is shown in FIG. 6, the sanitary napkin 1 manufactured by the manufacturing machine 10 has wings, and adhesive 4D is applied to the inside of the facing 4. The sanitary napkin 1 with wings may simply be referred to as sanitary napkin 1 in the present invention. Although the same numeral "1" is used to indicate both the sanitary napkin of the present embodiment and the conventional sanitary napkin shown in FIGS. 13 to 15, they are different from each other.

As the adhesive 4D is applied to all the inside of the facing of the sanitary napkin 1, positional slippage of the absorbent body is prevented and, hence, longitudinal and lateral leaks of catamenial flux and so on are prevented. Namely, longitudinal and lateral leaks of liquid such as catamenial flux can be prevented by the adhesive 4D.

The wrapping machine 100 will next be described.

As shown in FIG. 1, the wrapping machine 100 comprises a longitudinally folding unit 90, a slip-preventing-adhesive applying unit 110, an overlaying unit 120, a wing-folding unit 130, a hold-down-tape affixing unit 140, a film-sealing unit 150, and a cutting unit 160.

Figure 8:
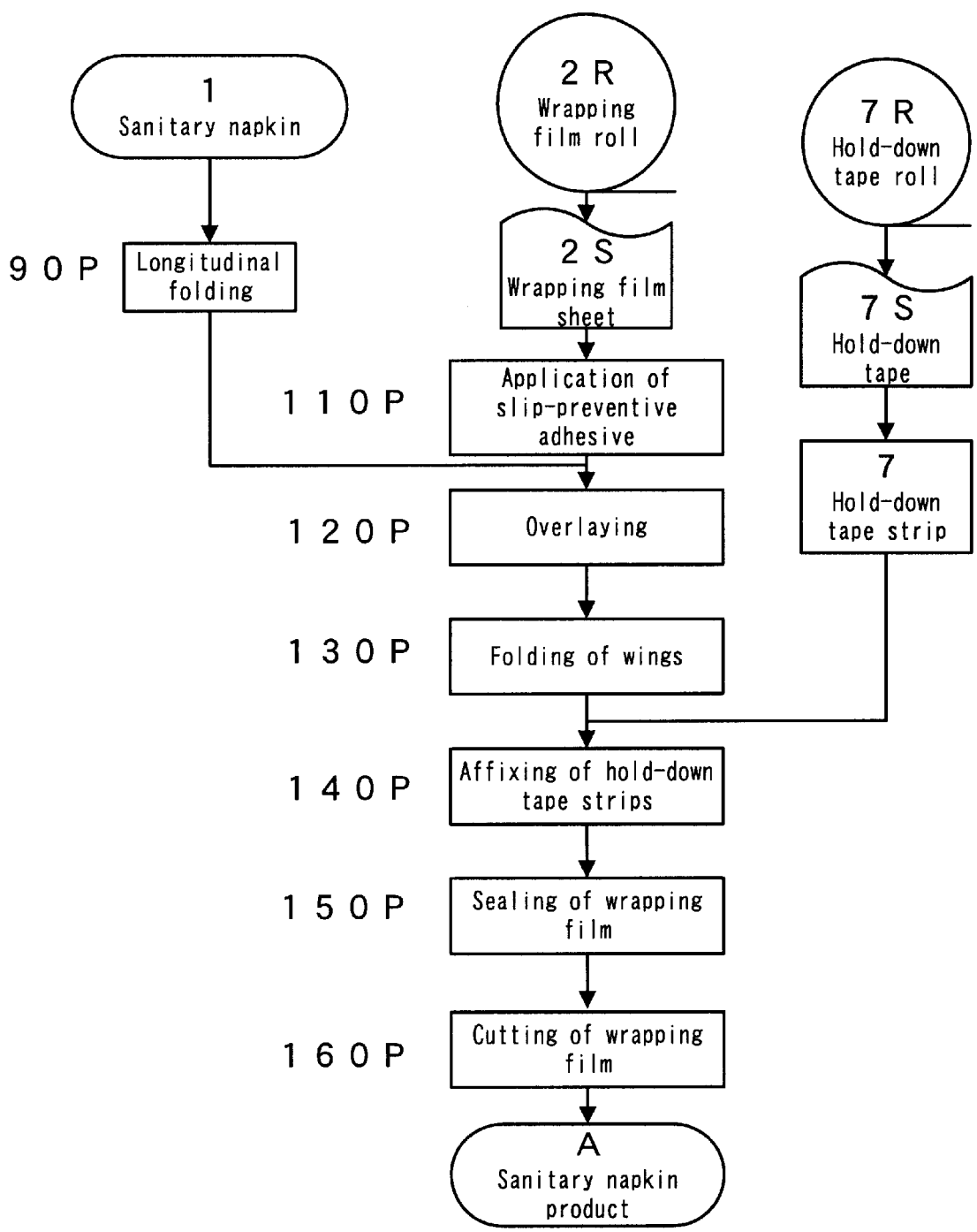
FIG. 8 is a flowchart showing the packing process of the sanitary napkin by the wrapping machine to produce the sanitary napkin product.

FIG. 8 is a flowchart of the wrapping process of the sanitary napkin 1 by the wrapping machine 100.

In FIG. 8, the signs 90P and 110P to 160P indicate the subprocesses by the units 90 and 110 to 160 of the wrapping machine 100.

The signs 2R and 2R indicate a wrapping film roll each. The signs 7R and 7R indicate a hold-down tape roll each. Two rolls are provided for each of the wrapping film sheet 2S and the hold-down tape 7S so that the material can be fed by either roll through a corresponding connecting device 9 without interruption.

Each wrapping film roll 2R consists of a wrapping film sheet 2S. The wrapping film sheet 2S is of a thermoplastic resin such as polyethylene, polyolefin, or vinyl chloride, and its one side is coated with silicone. Each hold-down tape roll 7R consists of a hold-down tape 7S, which is of a petrochemical.

The units 90 and 110 to 160 of the wrapping machine 100 will now be described.

The longitudinally folding unit 90 will first be described.

As shown in FIG. 5, the longitudinally folding unit 90 comprises a first folding mechanism 91 and a second folding mechanism 92. Each of the first and second folding mechanisms 91 and 92 comprises a pair of folding arms 93 and 93. Each folding arm 93 comprises a shaft and an arm. The base end of the arm is fixed to the shaft, both making a right angle.

The difference between the first and second folding mechanisms 91 and 92 is that the shafts of the first folding mechanism 91 are arranged horizontally, whereas those of the second folding mechanism 92 are arranged vertically.

Figure 9:
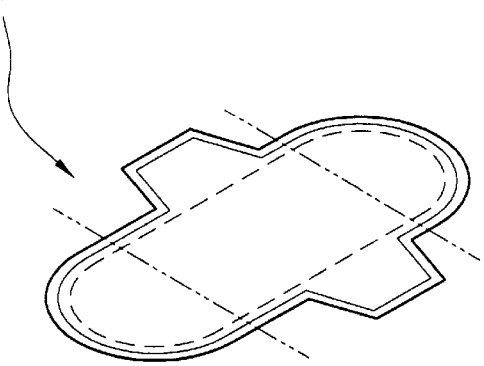
FIG. 9 (A) shows the initial state of the sanitary napkin.
Figure 9:
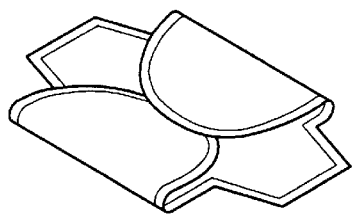
Figure 9:
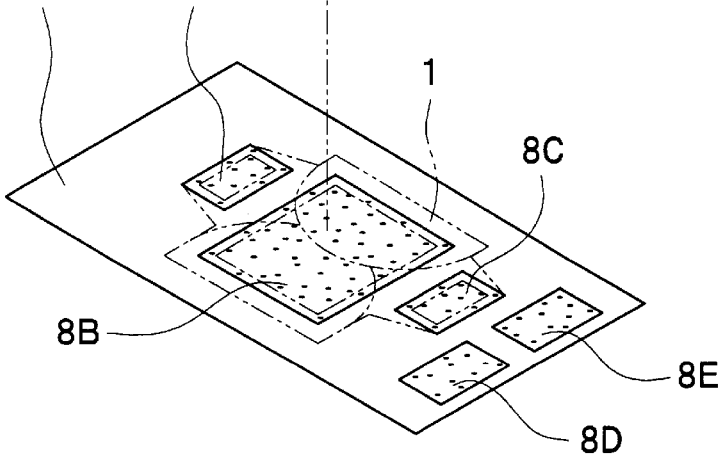

FIG. 9 shows two states of the sanitary napkin 1. FIG. 9 (A) shows the initial state; FIG. 9 (B), the subsequent state. The sanitary napkin 1 fed to the longitudinally folding unit 90 is folded in two at one of the two dash-double dot lines shown in FIG. 9 (A) and again folded in two at the other. In this way, both the longitudinal end parts of the sanitary napkin 1 are folded as shown in FIG. 9(B) (90P).

The slip-preventing-adhesive applying unit 110 will next be described.

FIG. 7 is a schematic perspective view of the wrapping machine 100. As shown in FIG. 7, the slip-preventing-adhesive applying unit 110 is a nozzle to apply slip-preventing adhesive 8A, 8B, 8C, 8D and 8E to the silicone-coated side of the wrapping film sheet 2S. Adhesives such as hot melt adhesive can be used as the adhesive 8A, 8B, 8C, 8D and 8E.

The signs 8A and 8C indicate adhesive to prevent the slippage of the wings of the sanitary napkin 1.

The sign 8B indicates adhesive to prevent the slippage of the middle part of the body of the sanitary napkin 1.

The signs 8D and 8E indicate adhesive to prevent the slippage of both the longitudinal end parts of the body of the sanitary napkin 1.

Because the packing film sheet 2S is running, slip-preventing adhesive 8A, 8B, 8C, 8D and 8E can be applied onto the packing film sheet 2S at regular intervals by ejecting adhesive regularly from the slip-preventing-adhesive applying unit 110 (110P).

The overlaying unit 120 will next be described.

In the overlaying unit 120, a feed roller 121 is provided freely rotatably in a vertical plane. As shown in FIG. 9 (B), in the overlaying unit 120, the slip-preventing adhesive 8A, 8B and 8C on the running wrapping film sheet 2S is overlaid with the sanitary napkin 1 which is folded by the longitudinally folding unit 90. Because pieces of the sanitary napkin 1 are sequentially fed and the wrapping film sheet 2S is running, pieces of the sanitary napkin 1 are sequentially put on the slip-preventing adhesive 8A, 8B and 8C on the wrapping film sheet 2S (120P).

A sealant-applying unit 111 is arranged above the running wrapping film sheet 2S. The sealant-applying unit 111 is a nozzle to apply sealant F, in the running direction, to the hem, on the opposite side of the slip-preventing adhesive 8D and 8E, of the running wrapping film sheet 2S.

Because the wrapping film sheet 2S is running, sealant F can be applied in a straight line to the hem of the wrapping film sheet 2S by ejecting sealant F continuously from the sealant-applying unit 111.

The sealant-applying unit 111 is not an essential constituent of the wrapping machine 100 of the manufacturing equipment of the sanitary napkin product of the present embodiment. However, applying sealant F to the wrapping film sheet 2S by the sealant-applying unit 111 is preferable because the wrapping film sheet 2S bearing sealant F can be sealed up by the wing-folding unit 130, which will be described later.

The wing-folding unit 130 will next be described.

As shown in FIGS. 7 and 8, the wing-folding unit 130 comprises a feed roller 131, a holding-down roller 132, and a folder 133. The feed roller 131 is known in the art and set freely rotatably in a vertical plane. The holding-down roller 132 is narrower than the wrapping film sheet 2S and provided freely rotatably in a vertical plane in such a position as presses down the center portion of the wrapping film sheet 2S between the feed roller 131 and the folder 133 to give it a flat-bottomed U shape as seen in the running direction of the wrapping film sheet 2S. The folder 133, a known device in the art, is to fold down the wings of the U-shaped wrapping film sheet 2S.

In this way, the wing-folding unit 130 folds the wrapping film sheet 2S together with the sanitary napkin 1, the sanitary napkin 1 inside the wrapping film sheet 2S, both the wings of the sanitary napkin 1 folded (130P).

The hold-down-tape affixing unit 140 will next be described.

The hold-down-tape affixing unit 140 comprises an affixing roller 141 and a cutter 142, the latter being an example of the "hold-down-tape cutting subunit" mentioned in claims of the present invention. The affixing roller 141 is provided freely rotatably in a vertical plane. The cutter 142 is to cut off the hold-down tape 7S and positioned adjoiningly to the affixing roller 141.

The affixing roller 141 rotates synchronously with the running speed of the wrapping film sheet 2S.

The hold-down tape 7S fed from a hold-down tape roll 7R is cut by the cutter 142 into hold-down tape strips 7, which stick to the periphery of the affixing roller 141. Each hold-down tape strip 7 carried on the turning affixing roller 141 comes into contact with, and sticks to, the wrapping film sheet 2S (140P).

The film-sealing unit 150 will next be described.

Figure 10:
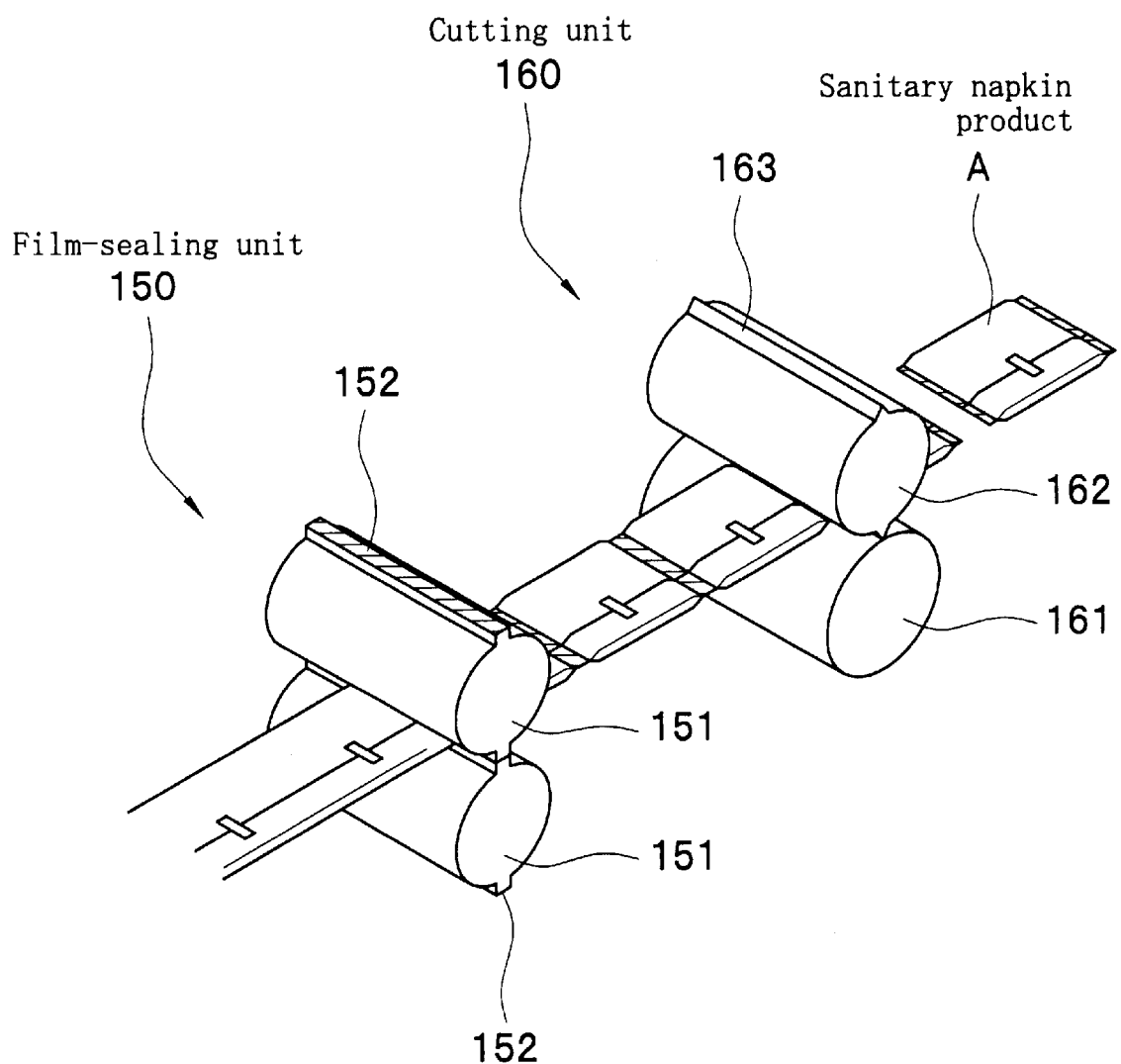
FIG. 10 is a schematic perspective view of the film-sealing unit and cutting unit of the wrapping machine.

FIG. 10 is a schematic perspective view of the film-sealing unit 150 and the cutting unit 160. As shown in FIG. 10, the film-sealing unit 150 comprises a pair of heat-sealing rollers 151 and 151. Each heat-sealing roller 151 has heating portions 152 on its periphery.

Although each heat-sealing roller 151 is provided with two heating portions 152 in FIG. 10, any number of heating portions 152 without particular limitation may be formed on the periphery of each heat-sealing roller 151.

The wrapping film sheet 2S is fed into between the paired heat-sealing rollers 151 and 151 to be heat-sealed in the intermediate portions between pieces of the sanitary napkin 1 (150P).

The cutting unit 160 will next be described.

The cutting unit 160 comprises freely rotatable, paired anvil roller 161 and rotary cutter 162. Cutter blades 163 are provided on the periphery of the rotary cutter 162.

The wrapping film sheet 2S runs into between the paired anvil roller 161 and rotary cutter 162 of the cutting unit 160. The wrapping film sheet 2S is running, and the anvil roller 161 and the rotary cutter 162 are rotating synchronously with the running speed of the wrapping film sheet 2S. Accordingly, each time a cutter blade 163 of the rotary cutter 162 meets the periphery of the anvil roller 161, the wrapping film sheet 2S is cut off to produce a piece of sanitary napkin product A (160P).

The width of the anvil roller 161 and rotary cutter 162 can be determined in accordance with the width of the wrapping film sheet 2S.

Given the above construction, the wrapping machine 100 wraps the sanitary napkin 1 in the wrapping film sheet 2S, as follows, to produce the sanitary napkin product A.

The pieces of the sanitary napkin 1 manufactured in sequence by the manufacturing machine 10 is fed to, and folded by, the longitudinally folding unit 90 (90P).

On the other hand, the slip-preventing-adhesive applying unit 110 applies adhesive 8A, 8B, 8C, 8D and 8E to the wrapping film sheet 2S fed from a wrapping film roll 2R (110P).

The adhesive 8A, 8B, 8C on the running wrapping film sheet 2S is overlaid with the sanitary napkin 1 (120P).

The sealant-applying unit 111 applies sealant F, in a straight line in the running direction of the wrapping film sheet 2S, to the hem, on the opposite side of the slip-preventing adhesive 8D and 8E, of the wrapping film sheet 2S.

The holding-down roller 132 of the wing-folding unit 130 forms the running wrapping film sheet 2S together with the sanitary napkin 1 into a flat-bottomed U shape as seen in the running direction of the wrapping film sheet 2S, the sanitary napkin 1 inside the wrapping film sheet 2S, both the wings of the sanitary napkin 1 folded upward. Then, the folder 133 folds down the wing, on the side of the slip-preventing adhesive 8D and 8E, of the U consisting of the wrapping film sheet 2S and the sanitary napkin 1. Immediately thereafter, the folder 133 folds down the wing, on the side of the sealant F, of the U consisting of the wrapping film sheet 2S and the sanitary napkin 1 (130P). Thus, the wrapping film sheet 2S is sealed up by the sealant F.

The cutter 142 of the hold-down-tape affixing unit 140 cuts the hold-down tape 7S fed from a hold-down tape roll 7R into hold-down tape strips 7, which stick to the periphery of the affixing roller 141. The affixing roller 141 turns and affixes the hold-down tape strips 7 onto the running wrapping film sheet 2S at regular intervals (140P).

The wrapping film sheet 2S is fed into between the paired heat-sealing rollers 151 and 151, and the intermediate portions between pieces of the sanitary napkin 1 are heat-sealed sequentially (150P).

Lastly, the wrapping film sheet 2S is fed into between the paired anvil roller 161 and rotary cutter 162. Each time a cutter blade 163 meets the periphery of the anvil roller 161, the wrapping film sheet 2S is cut off to produce a piece of the sanitary napkin product A (160P).

In this way, pieces of the sanitary napkin 1 with wings are wrapped sequentially in a wrapping film sheet 2S, and pieces of the sanitary napkin product A are produced sequentially.

Figure 11:
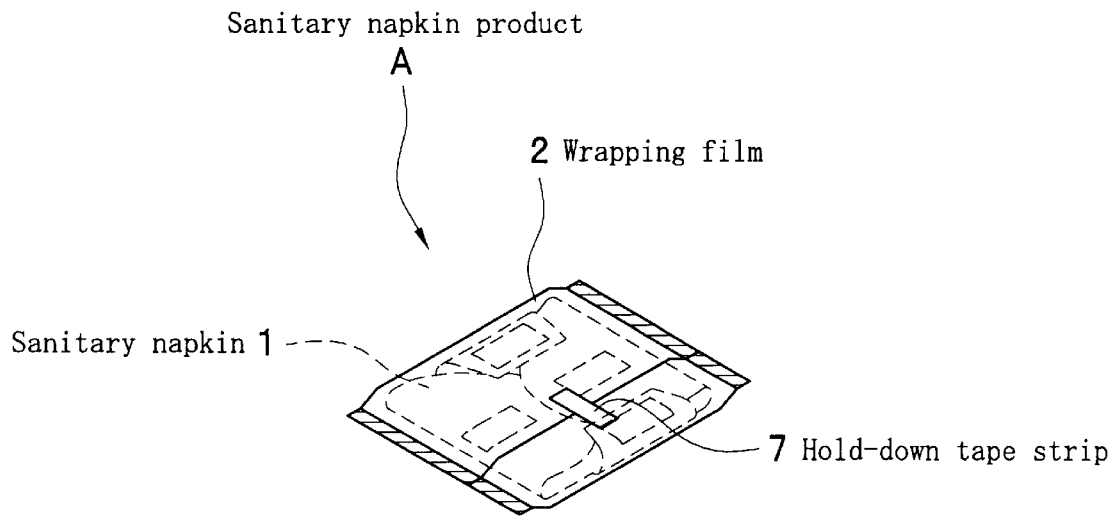
FIG. 11 (I) is a schematic perspective view of the sanitary napkin product.
Figure 11:
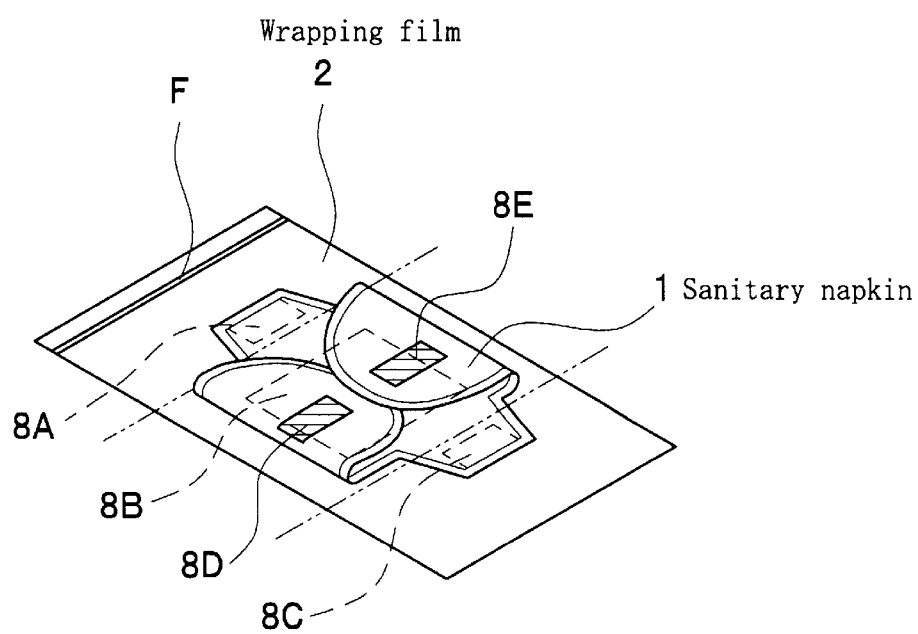

FIG. 11 (I) is a schematic perspective view of the sanitary napkin product A manufactured by the manufacturing equipment of the present embodiment; FIG. 11 (II), a schematic perspective view of the sanitary napkin product A, of which the wrapping film 2 is open. As shown in FIG. 11 (I), the sanitary napkin product A is a sanitary napkin 1 with wings which is wrapped entirely in a wrapping film 2. The inside of the wrapping film 2 is coated with silicone. A coat of the slip-preventing adhesive 8A, 8B, 8C, 8D and 8E, which comes easily off silicone coats, is formed between the silicone-coated side of the wrapping film sheet 2S and the back of the sanitary napkin 1.

To take out the sanitary napkin 1 from the wrapping film 2, pull the hold-down tape 7, and the wrapping film 2 will tears along the portion of sealant F and further along the heat-sealed hems.

In the meantime, the adhesive 8D and 8E on the wrapping film 2 comes off the wrapping film 2 to stay on the backs of the longitudinal end parts of the sanitary napkin 1. Then, tear the sanitary napkin 1 off the wrapping film 2, and the adhesive 8A and 8C and the adhesive 8B on the wrapping film 2 will come off the wrapping film 2 to stay on the backs of the wings, and the back of the middle part of the body, of the sanitary napkin 1, respectively. Thus, when the sanitary napkin 1 is used, the adhesive 8A, 8B, 8C, 8D and 8E on the back of the sanitary napkin 1 adheres to underwear to prevent the positional slippage of the sanitary napkin 1.

Besides, no peeling-off paper is used in the sanitary napkin product A, which reduces the quantity of wastes and the production cost of the sanitary napkin product A.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What I claim is:

1. A sanitary-napkin-product manufacturing equipment comprising:
    a manufacturing machine to manufacture a sanitary napkin with wings; and
    a wrapping machine to apply slip-preventing adhesive, which comes easily off silicone coats, to the back of the sanitary napkin and wrap the sanitary napkin in a wrapping film, of which the inside is coated with silicone, to produce a sanitary napkin product.

2. A sanitary-napkin-product manufacturing equipment as claimed in claim 1 of which the manufacturing machine, wherein a continuous facing sheet fed from its roll, a continuous absorbent sheet fed from its roll, and a continuous lining sheet fed from its roll run respectively, comprises:
    an absorbent-body cutout unit which cuts out absorbent bodies one after another at intervals in the running direction from the running absorbent sheet;
    a lining-sheet-adhesive applying unit which applies adhesive to the running lining sheet continuously in the running direction;
    a facing-sheet-adhesive applying unit which applies adhesive to the running facing sheet continuously in the running direction;
    a sandwiching unit which puts the absorbent bodies sequentially between the running facing sheet and the running lining sheet and puts them together to make a sanitary napkin sheet;
    a heat-sealing unit which seals with heat the portion inside and along the outline—of the portion including the absorbent body which becomes the sanitary napkin; and
    a sanitary-napkin cutout unit which cuts out pieces of the sanitary napkin sheet one after another at intervals from the sanitary napkin sheet holding the absorbent bodies inside.

3. A sanitary-napkin-product manufacturing equipment as claimed in claim 2 wherein:
    the absorbent-body cutout unit comprises paired anvil roller and die-cut roller;
    the die-cut roller has cutter blades on its periphery to cut out absorbent bodies; and
    the absorbent sheet runs into between the paired anvil roller and die-cut roller for absorbent bodies to be cut out one after another.

4. A sanitary-napkin-product manufacturing equipment as claimed in claim 2 or 3 wherein:

the heat-sealing unit comprises paired anvil roller and heat-sealing roller;

the heat-sealing roller has nonheating portions on its periphery, each a little smaller than the sanitary napkin; and the sanitary napkin sheet runs into between the paired anvil roller and heat-sealing roller.

5. A sanitary-napkin product manufacturing equipment as claimed in claim 2 or 3 wherein:

the sanitary-napkin cutout unit comprises paired anvil roller and die-cut roller;

the die-cut roller has cutter blades on its periphery; and the sanitary-napkin sheet runs into between the paired anvil roller and die-cut roller for pieces of the sanitary napkin to be cut out one after another.

6. A sanitary-napkin-product manufacturing equipment as claimed in claim 1 of which the wrapping machine comprises:

a longitudinally folding unit which folds both the longitudinal end parts of the body of the sanitary napkin onto the front side of the sanitary napkin;

a slip-preventing-adhesive applying unit, in front of which a continuous wrapping film sheet with one side coated with silicone fed from its roll runs, and which applies slip-preventing adhesive to the silicone-coated side of the wrapping film sheet at intervals in the running direction;

an overlaying unit which puts the sanitary napkin on the slip-preventing adhesive on the running wrapping film sheet;

a wing-folding unit which folds the running wrapping film sheet together with the sanitary napkin in the direction of width of the wrapping film sheet, the sanitary napkin inside the wrapping film sheet, both the wings of the sanitary napkin folded;

a hold-down-tape affixing unit which cuts a continuous hold-down tape fed from its roll into hold-down tape strips and affixes them at intervals in the running direction onto both the hems overlapping each other of the wrapping film sheet;

a film-sealing unit which seals with heat the intermediate portions between pieces of the sanitary napkin at intervals in the running direction; and a cutting unit which cuts off the wrapping film sheet in the intermediate portions between pieces of the sanitary napkin.

7. A sanitary-napkin-product manufacturing equipment as claimed in claim 6 wherein:

the slip-preventing-adhesive applying unit applies slip-preventing adhesive to such parts of the silicone-coated side of the running wrapping film sheet as correspond positionally to the middle part and longitudinal end parts of the body, and both the wings, of the sanitary napkin; and the overlaying unit puts the sanitary napkin with its longitudinal end parts folded on the slip-preventing adhesive on the wrapping film sheet, the back of the sanitary napkin coming into contact with the slip-preventing adhesive, the middle part of the body and the wings of the sanitary napkin corresponding positionally to the slip-preventing-adhesive-applied counterparts of the wrapping film sheet.

8. A sanitary-napkin-product manufacturing equipment as claimed in claim 6 or 7 wherein the wing-folding unit comprises:

a feed roller which is set freely rotatably in a vertical plane;

a holding-down roller which is narrower than the wrapping film sheet, positioned lower than the feed roller, and set freely rotatably; and a folder, the wrapping film sheet running on the feed roller, under the holding-down roller, and through the folder to be folded widthwise continuously, the longitudinal end parts of the body of the sanitary napkin overlaid with the slip-preventing-adhesive-applied counterparts of the wrapping film sheet.

9. A sanitary-napkin-product manufacturing equipment as claimed in claim 6 or 7 of which the hold-down-tape affixing unit comprises:

a hold-down-tape cutting subunit which cuts the hold-down tape into hold-down tape strips one after another; and an affixing roller which affixes the hold-down tape strips to the hems of the running wrapping film sheet.

* * * * *